United States Patent [19]

Livesey

[11] Patent Number: 5,354,942
[45] Date of Patent: Oct. 11, 1994

[54] INBRED CORN LINE PHEM9

[75] Inventor: James M. Livesey, Woodstock, Canada

[73] Assignee: Pioneer Hi-Bred International, Inc., Des Moines, Iowa

[21] Appl. No.: 12,665

[22] Filed: Feb. 3, 1993

[51] Int. Cl.$^5$ .......................... A01H 5/00; A01H 4/00; C12N 5/04

[52] U.S. Cl. ..................................... 800/200; 800/250; 800/DIG. 56; 435/240.4; 435/240.49; 435/240.5

[58] Field of Search ................ 435/172.1, 172.3, 240.4, 435/240.49, 240.5; 536/27; 800/200, 250, DIG. 52, DIG. 56; 935/18; 47/58.03, DIG. 1

[56] References Cited

U.S. PATENT DOCUMENTS 4,812,599  3/1989  Segebart ................................. 800/1

FOREIGN PATENT DOCUMENTS 160390  11/1985  European Pat. Off. .

OTHER PUBLICATIONS

Hallauer et al. 1988. *In* Corn and Corn Improvement. Ch. 8:463–564. Sprague et al., eds.
Edallo et al. 1981. Maydica. 26: 39–56.
Phillips et al. 1988. *In* Corn and Corn Improvement. Ch. 5: 345–387. Sprague et al., eds.
Meghji et al. 1984. Crop Science. 24: 545–549.
Wright. 1980. *In* Hybridization Of Crop Plants. Ch. 8: 161–176. Fehr et al., eds.
Wych. 1988. *In* Corn and Corn Improvement. Ch. 9: 565–607. Sprague et al., eds.
Conger, B. V., et al., "Somatic Embryogenesis From Cultured Leaf Segments of Zea Mays", Plant Cell Reports, 6:345–347 (1987).
Rao, K. V., et al., "Somatic Embryogenesis in Glume Callus Cultures", Osmania University, Hyderabad, India.
Songstad, D. D., et al., "Effect of ACC (1–aminocyclopropane-1-carboxylic acid), Silver Nitrate & Norbornadiene on Plant Regeneration From Maize Callus Cultures", Plant Cell Reports, 7:262–265 (1988).
Duncah, D. R., et al., "The Production of Callus Capable of Plant Regeneration From Immature Embryos of Numerous Zea mays Genotype", Planta, 165:322–332 (1985).
Poehlman, J. M., "Breeding Field Crops" Third Edition (1987), AVI Publishing Company, Inc., pp. 237–247.
Green, et al., "Plant Regeneration From Tissue Cultures In Maize" Crop Science, vol. 15, pp. 417–421 (1975).
Green, C. E., et al., "Plant Regeneration in Tissue Cultures of Maize" Maize for Biological Research pp. 367–372 (1982).
Sass, "Morphology", In Corn & Corn Improvement. ASA Publication. Madison, Wisconsin, pp. 89–110. (1977).
Troyer, et al., "Selection for Early Flowering in Corn: 10 Late Synthetics". Crop Science, vol. 25, pp. 695–697 (1985).
Umbeck, et al. "Reversion of Male-Sterile T-Cytoplasm Maize to Male Fertility in Tissue Culture" Crop Science. vol. 23, pp. 584–588. (1983).
Tomes, et al., "The Effect of Parental Genotype on Initiation of Embryogenic Callus from Elite Maize (Zea mays L.) germplasm". Theor. Appl. Genet. 70. pp. 505–509. (1985).

*Primary Examiner*—Gary Benzion
*Assistant Examiner*—Erich E. Veitenheimer
*Attorney, Agent, or Firm*—Pioneer Hi-Bred International, Inc.

[57] ABSTRACT

According to the invention, there is provided an inbred corn line, designated PHEM9. This invention thus relates to the plants and seeds of inbred corn line PHEM9 and to methods for producing a corn plant produced by crossing the inbred line PHEM9 with itself or with another corn plant. This invention further relates to hybrid corn seeds and plants produced by crossing the inbred line PHEM9 with another corn line or plant.

6 Claims, 1 Drawing Sheet

INBRED CORN LINE PHEM9

FIELD OF THE INVENTION

This invention is in the field of corn breeding, specifically relating to an inbred corn line designated PHEM9.

BACKGROUND OF THE INVENTION

Plant Breeding

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant.

Corn plants (*Zea mays* L.) can be bred by both self-pollination and cross-pollination techniques. Corn has separate male and female flowers on the same plant, located on the tassel and the ear, respectively. Natural pollination occurs in corn when wind blows pollen from the tassels to the silks that protrude from the tops of the incipient ears.

The development of a hybrid corn variety involves three steps: (1) the selection of plants from various germplasm pools; (2) the selfing of the selected plants for several generation to produce a series of inbred lines, which, although different from each other, breed true and are highly uniform; and (3) crossing the selected inbred lines with unrelated inbred lines to produce the hybrid progeny ($F_1$). During the inbreeding process in corn, the vigor of the lines decreases. Vigor is restored when two unrelated inbred lines are crossed to produce the hybrid progeny. An important consequence of the homozygosity and homogeneity of the inbred lines is that the hybrid between any two inbreds will always be the same. Once the inbreds that give a superior hybrid have been identified, the hybrid seed can be reproduced indefinitely as long as the homogeneity of the inbred parents is maintained.

The objective of commercial maize inbred line development programs is to develop new inbred lines that combine to produce high grain yields and superior agronomic performance in hybrid combination. The primary trait breeders seek is yield. However, other major agronomic traits are of importance in hybrid combination and have an impact on yield or otherwise provide superior performance in hybrid combinations. Such traits include percent grain moisture at harvest, relative maturity, resistance to stalk breakage, resistance to root lodging, grain quality, and disease and insect resistance. In addition the lines per se must have acceptable performance for parental traits such as seed yields, kernel sizes, pollen production, all of which affect ability to provide parental lines in sufficient quantity and quality for hybridization. These traits have been shown to be under genetic control and many if not all of the traits are affected by multiple genes. Thus, to be selected as an inbred line, the inbred must be able to combine such that the desired traits are passed to the hybrid and also be able to satisfy production requirements as a parental line.

Pedigree Breeding

The pedigree method of breeding is the mostly widely used methodology for new inbred line development.

In general terms this procedure consists of crossing two inbred lines to produce the non-segregating $F_1$ generation, and self pollination of the $F_1$ generation to produce the $F_2$ generation that segregates for all factors for which the inbred parents differ. An example of this process is set forth below. Variations of this generalized pedigree method are used, but all these variations produce a segregating generation which contains a range of variation for the traits of interest.

EXAMPLE 1

Hypothetical example of pedigree breeding program

Consider a cross between two inbred lines that differ for alleles at five loci.
The parental genotypes are:

| Parent 1 | A | b | C | d | e | F/A | b | C | d | e | F |
| Parent 2 | a | B | c | D | E | f/a | B | c | D | E | f | the $F_1$ from a cross between these two parents is:

| $F_1$ | A b C d e F/a B c D E f |

Selfing $F_1$ will produce an $F_2$ generation including the following genotypes:

| A | B | c | D | E | f/a | b | C | d | e | F |
| A | B | c | D | e | f/a | b | C | d | E | F |
| A | B | c | D | e | f/a | b | C | d | e | F |
| . |
| . |
| . |

The number of genotypes in the $F_2$ is $3^6$ for six segregating loci (729) and will produce $(2^6) - 2$ possible new inbreds, (62 for six segregating loci).

Each inbred parent which is used in breeding crosses represents a unique combination of genes, and the combined effects of the genes define the performance of the inbred and its performance in hybrid combination. There is published evidence (Smith, O.S., J.S.C. Smith, S. L. Bowen, R. A. Tenborg and S. J. Wall, TAG 80:833–840 (1990)) that each of these lines are different and can be uniquely identified on the basis of genetically-controlled molecular markers.

It has been shown (Hallauer, Arnel R. and Miranda, J.B. Fo. *Quantitative Genetics in Maize Breeding*, Iowa State University Press, Ames Iowa (1981)) that most traits of economic value in maize are under the genetic control of multiple genetic loci, and that there are a large number of unique combinations of these genes present in elite maize germplasm. If not, genetic progress using elite inbred lines would no longer be possible. Studies by Duvick and Russell (Duvick, D.N., *Maydica* 37:69–79 (1992); Russell, W.A., *Maydica* XXIX:375–390 (1983)) have shown that over the last 50 years the rate of genetic progress in commercial hybrids has been between 1 and 2% per year.

The number of genes affecting the trait of primary economic importance in maize, grain yield, has been estimated to be in the range of 10–1000. Inbred lines which are used as parents for breeding crosses differ in the number and combination of these genes. These factors make the plant breeder's task more difficult. Compounding this is evidence that no one line contains the favorable allele at all loci, and that different alleles have different economic values depending on the genetic background and field environment in which the hybrid is grown. Fifty years of breeding experience shows that there are many genes affecting grain yield and each of these has a relatively small effect on this trait. The effects are small compared to breeders' ability to measure grain yield differences in evaluation trials. Therefore, the parents of the breeding cross must differ at several of these loci so that the genetic differences in the progeny will be large enough that breeders can develop a line that increases the economic worth of its hybrids over that of hybrids made with either parent.

If the number of loci segregating in a cross between two inbred lines is n, the number of unique genotypes in the $F_2$ generation is $3^n$ (Table 2) and the number of unique inbred lines from this cross is $\{(2^n)-2\}$. Only a very limited number of these combinations are useful. Only about 1 in 10,000 of the progeny from $F_2$'s are commercially useful.

By way of example, if it is assumed that the number of segregating loci in $F_2$ is somewhere between 20 and 50, and that each parent is fixed for half the favorable alleles, it is then possible to calculate approximate probabilities of finding an inbred that has the favorable allele at $\{(n/2)+m\}$ loci, where n/2 is the number of favorable alleles in each of the parents and m is the number of additional favorable alleles in the new inbred. See Example 2 below. The number m is assumed to be greater than three because each allele has so small an effect that evaluation techniques are not sensitive enough to detect differences due to three or less favorable alleles. The probabilities in Example 2 are on the order of $10^{-5}$ or smaller and they are the probabilities that at least one genotype with $(n/2)+m$ favorable alleles will exist.

To put this in perspective the number of plants grown on 60 million acres (approximate US corn acreage) at 25000 plants/acre is $1.5 \times 10^{12}$.

EXAMPLE 2

Probability of finding an inbred with m of n favorable alleles.

Assume each parent has n/2 of the favorable alleles and only ½ of the combinations of loci are economically useful.

| no. of segregating loci (n) | No. favorable alleles in Parents (n/2) | No. additional favorable alleles in new inbred | Probability that genotype occurs* |
| --- | --- | --- | --- |
| 20 | 10 | 14 | $3 \times 10^{-5}$ |
| 24 | 12 | 16 | $2 \times 10^{-5}$ |
| 28 | 14 | 18 | $1 \times 10^{-5}$ |
| 32 | 16 | 20 | $8 \times 10^{-6}$ |
| 36 | 18 | 22 | $5 \times 10^{-6}$ |
| 40 | 20 | 24 | $3 \times 10^{-6}$ |
| 44 | 22 | 26 | $2 \times 10^{-6}$ |
| 48 | 24 | 28 | $1 \times 10^{-6}$ |

*Probability that a useful combination exists, does not include the probability of identifying this combination if it does exist.

The possibility of having a usably high probability of being able to identify this genotype based on replicated field testing would be most likely smaller than this, and is a function of how large a population of genotypes is tested and how testing resources are allocated in the testing program.

At Pioneer Hi-Bred International, a typical corn research station has a staff of four, and 20 acres of breeding nursery. Those researchers plant those 20 acres with 25,000 nursery rows, 15,000 yield test plots in 10–15 yield test sites, and one or two disease-screening nurseries. Employing a temporary crew of 20 to 30 pollinators, the station makes about 65,000 hand pollinations per growing season. Thus, one of the largest plant breeding programs in the world does not have a sufficiently large breeding population to be able to rely upon "playing the numbers" to obtain successful research results. Nevertheless, Pioneer's breeders at each station produce from three to ten new inbreds which are proposed for commercial use each year. Over the 32 Pioneer research stations in North America, this amounts to from about 100 to 300 new inbreds proposed for use, and less than 50 and more commonly less than 30 of these inbreds that actually satisfy the performance criteria for commercial use.

This is a result of plant breeders using their skills, experience, and intuitive ability to select inbreds having the necessary qualities.

SUMMARY OF THE INVENTION

According to the invention, there is provided a novel inbred corn line, designated PHEM9. This invention thus relates to the seeds of inbred corn line PHEM9, to the plants of inbred corn line PHEM9, and to methods for producing a corn plant produced by crossing the inbred line PHEM9 with itself or another corn line. This invention further relates to hybrid corn seeds and plants produced by crossing the inbred line PHEM9 with another corn line.

DEFINITIONS

In the description and examples that follow, a number of terms are used herein. In order to provide a clear and consistent understanding of the specification and claims, including the scope to be given such terms, the following definitions are provided. ABS is in absolute terms and % MN is percent of the mean for the experiments in which the inbred or hybrid was grown.

BAR PLT=BARREN PLANTS. The percent of plants per plot that were not barren (lack ears).

BRT STK=BRITTLE STALKS. This is a measure of the stalk breakage near the time of pollination, and is an indication of whether a hybrid or inbred would snap or break near the time of flowering under severe winds. Data are presented as percentage of plants that did not snap.

BU ACR=YIELD (BUSHELS/ACRE). Actual yield of the grain at harvest in bushels per acre adjusted to 15.5% moisture.

DRP EAR=DROPPED EARS. A measure of the number of dropped ears per plot and represents the percentage of plants that did not drop ears prior to harvest.

EAR HT=EAR HEIGHT. The ear height is a measure from the ground to the highest placed developed ear node attachment and is measured in inches.

EAR SZ=EAR SIZE. A 1 to 9 visual rating of ear size. The higher the rating the larger the ear size.

EST CNT=EARLY STAND COUNT. This is a measure of the stand establishment in the spring and represents the number of plants that emerge on a per plot basis for the inbred or hybrid.

GDU SHD=GDU TO SHED. The number of growing degree units (GDUs) or heat units required for an inbred line or hybrid to have approximately 50 percent of the plants shedding pollen and is measured from the time of planting. Growing degree units are calculated by the Barger Method, where the heat units for a 24-hour period are:

$$GDU = \frac{(\text{Max. temp.} + \text{Min. temp})}{2}$$

The highest maximum temperature used is 86° F. and the lowest minimum temperature used is 50° F. For each inbred or hybrid it takes a certain number of GDUs to reach various stages of plant development.

GDU SLK=GDU TO SILK. The number of growing degree units required for an inbred line or hybrid to have approximately 50 percent of the plants with silk emergence from time of planting. Growing degree units are calculated by the Barger Method as given in GDU SHD definition.

GRN APP=GRAIN APPEARANCE. This is a 1 to 9 rating for the general appearance of the shelled grain as it is harvested based on such factors as the color of the harvested grain, any mold on the grain, and any cracked grain. High scores indicate good grain quality.

MST=HARVEST MOISTURE. The moisture is the actual percentage moisture of the grain at harvest.

PLT HT=PLANT HEIGHT. This is a measure of the height of the plant from the ground to the tip of the tassel in inches.

POL SC=POLLEN SCORE. A 1 to 9 visual rating indicating the amount of pollen shed. The higher the score the more pollen shed.

POL WT=POLLEN WEIGHT. This is calculated by dry weight of tassels collected as shedding commences minus dry weight from similar tassels harvested after shedding is complete.

It should be understood that the inbred can, through routine manipulation of cytoplasmic factors, be produced in a cytoplasmic male-sterile form which is otherwise phenotypically identical to the male-fertile form.

PRM=PREDICTED RM. This trait, predicted relative maturity (RM), is based on the harvest moisture of the grain. The relative maturity rating is based on a known set of checks and utilizes standard linear regression analyses and is referred to as the Comparative Relative Maturity Rating System which is similar to the Minnesota Relative Maturity Rating System.

RT LDG=ROOT LODGING. Root lodging is the percentage of plants that do not root lodge; plants that lean from the vertical axis at an approximately 30° angle or greater would be counted as root lodged.

SCT GRN=SCATTER GRAIN. A 1 to 9 visual rating indicating the amount of scatter grain (lack of pollination or kernel abortion) on the ear. The higher the score the less scatter grain.

SDG VGR=SEEDLING VIGOR. This is the visual rating (1 to 9) of the amount of vegetative growth after emergence at the seedling stage (approximately five leaves). A higher score indicates better vigor.

SEL IND=SELECTION INDEX. The selection index gives a single measure of the hybrid's worth based on information for up to five traits. A corn breeder may utilize his or her own set of traits for the selection index. One of the traits that is almost always included is yield. The selection index data presented in the tables represent the mean value averaged across testing stations.

STA GRN=STAY GREEN. Stay green is the measure of plant health near the time of black layer formation (physiological maturity). A high score indicates better late-season plant health.

STK CNT=NUMBER OF PLANTS. This is the final stand or number of plants per plot.

STK LDG=STALK LODGING. This is the percentage of plants that did not stalk lodge (stalk breakage) as measured by either natural lodging or pushing the stalks and determining the percentage of plants that break below the ear.

TAS BLS=TASSEL BLAST. A 1 to 9 visual rating was used to measure the degree of blasting (necrosis due to heat stress) of the tassel at time of flowering. A 1 would indicate a very high level of blasting at time of flowering, while a 9 would have no tassel blasting.

TAS SZ=TASSEL SIZE. A 1 to 9 visual rating was used to indicate the relative size of the tassel. The higher the rating the larger the tassel.

TAS WT=TASSEL WEIGHT. This is the average weight of a tassel (grams) just prior to pollen shed.

TEX EAR=EAR TEXTURE. A 1 to 9 visual rating was used to indicate the relative hardness (smoothness of crown) of mature grain. A 1 would be very soft (extreme dent) while a 9 would be very hard (flinty or very smooth crown).

TILLER=TILLERS. A count of the number of tillers per plot that could possibly shed pollen was taken. Data is given as percentage of tillers: number of tillers per plot divided by number of plants per plot.

TST WT=TEST WEIGHT (UNADJUSTED). The measure of the weight of the grain in pounds for a given volume (bushel).

TST WTA=TEST WEIGHT ADJUSTED. The measure of the weight of the grain in pounds for a given volume (bushel) adjusted for percent moisture.

YLD=YIELD. It is the same as BU ACR ABS.

YLD SC=YIELD SCORE. A 1 to 9 visual rating was used to give a relative rating for yield based on plot ear piles. The higher the rating the greater visual yield appearance.

MDM CPX=Maize Dwarf Mosaic Complex (MDMV=Maize Dwarf Mosaic Virus & MCDV=Maize Chlorotic Dwarf Virus): Visual rating (1–9 score) where a "1" is very susceptible and a "9" is very resistant.

SLF BLT=Southern Leaf Blight (*Bipolaris maydis, Helminthosporium maydis*): Visual rating (1–9 score) where a "1" is very susceptible and a "9" is very resistant.

NLF BLT=Northern Leaf Blight (*Exserohilum turcicum, H. turcicum*): Visual rating (1–9 score) where a "1" is very susceptible and a "9" is very resistant.

COM RST=Common Rust (*Puccinia sorghi*): Visual rating (1–9 score) where a "1" is very susceptible and a "9" is very resistant.

GLF SPT=Gray Leaf Spot (*Cercospora zeae-maydis*): Visual rating (1–9 score) where a "1" is very susceptible and a "9" is very resistant.

STW WLT=Stewart's Wilt (*Erwinia stewartii*): Visual rating (1–9 score) where a "1" is very susceptible and a "9" is very resistant.

HD SMT=Head Smut (*Sphacelotheca reiliana*): Percentage of plants that did not have infection.

EAR MLD=General Ear Mold: Visual rating (1–9 score) where a "1" is very susceptible and a "9" is very resistant. This is based on overall rating for ear mold of mature ears without determining specific mold organism, and may not be predictive for a specific ear mold.

ECB DPE=Dropped ears due to European Corn Borer (*Ostrinia nubilalis*): Percentage of plants that did not drop ears under second brood corn borer infestation.

ECB 2SC=European Corn Borer Second Brood (*Ostrinia nubilalis*): Visual rating (1–9 score) of post flowering damage due to infestation by European Corn Borer. A "1" is very susceptible and a "9" is very resistant.

ECB 1LF=European Corn Borer First Brood (*Ostrinia nubilalis*): Visual rating (1–9 score) of pre-flowering leaf feeding by European Corn Borer. A "1" is very susceptible and a "9" is very resistant.

DETAILED DESCRIPTION OF THE INVENTION

This inbred corn line PHEM9 contributes good root lodging resistance which is a problem with inbreds adapted to the northern regions. Compared to inbreds for the northern region which also have acceptable yield, this inbred stands well and has shown good resistance during especially difficult root lodging years. In addition, it has long and wide leaves for an inbred with this maturity, providing more leaf area index.

Inbred corn line PHEM9 is a yellow, dent corn inbred that provides an acceptable female parental line in crosses for producing first generation F1 corn hybrids. PHEM9 is best adapted to the Northeast region of the United States. The inbred has very good early growth, excellent staygreen, solid stalk strength and excellent roots and is high yielding. PHEM9 is unique in that it has long but wide, very green, semi-erect leaves. PHEM9 has excellent female yield and does well in hybrid production fields, therefore, ample seed should be available for farmers year after year.

The inbred has shown uniformity and stability within the limits of environmental influence for all the traits as described in the Variety Description Information (Table 1) that follows. Most of the data in the Variety Description information was collected at Johnston, Iowa. The inbred has been self-pollinated and ear-rowed a sufficient number of generations with careful attention paid to uniformity of plant type to ensure homozygosity and phenotypic stability. The line has been increased both by hand and in isolated fields with continued observation for uniformity. No variant traits have been observed or are expected in PHEM9.

Inbred corn line PHEM9, being substantially homozygous, can be reproduced by planting seeds of the line, growing the resulting corn plants under self-pollinating or sib-pollinating conditions with adequate isolation, and harvesting the resulting seed, using techniques familiar to the agricultural arts.

TABLE 1

VARIETY DESCRIPTION INFORMATION
INBRED = PHEM9

| Type: Dent | Region Best Adapted: NORTH EAST |
|---|---|
| A. Maturity: Average across maturity zones. Zone: | 0 |
| Heat Unit Shed: | 1280 |
| Heat Unit Silk: | 1310 |
| No. Reps: | 51 |

$$\text{HEAT UNITS} = \frac{[\text{Max. Temp. } (\leq 86° \text{ F.}) + \text{Min. Temp } (\geq 50° \text{ F.})]^*}{2} - 50$$

*If maximum is greater than 86 degrees fahrenheit, then 86 is used and if minimum is less than 50, then 50 is used. Heat units accumulated daily and can not be less than 0.

B. Plant Characteristics:

| | |
|---|---|
| Plant height (to tassel tip): | 191 cm |
| Length of top ear internode: | 11 cm |
| Number of ears per stalk: | SINGLE |
| Ear height (to base of top ear): | 60 cm |
| Number of tillers: | 1–2 |
| Cytoplasm type: | NORMAL |

C. Leaf:

| | |
|---|---|
| Color: | (B14) DARK GREEN |
| Angle from Stalk: | 30–60 degrees |
| Marginal Waves: | (WF9) FEW |
| Number of Leaves (mature plants): | 16 |
| Sheath Pubescence: | (W22) LIGHT |
| Longitudinal Creases: | (OH56A) FEW |
| Length (Ear node leaf): | 77 cm |
| Width (widest point, ear node leaf): | 10 cm |

D. Tassel:

| | |
|---|---|
| Number lateral branches: | 6 |
| Branch Angle from central spike: | >45 degrees |
| Pollen Shed: | Medium based on Pollen Yield Test (114% of experiment means) |
| Peduncle Length (top leaf to basal branches): | 18 cm |
| Anther Color: | RED |
| Glume Color: | GREEN |

E. Ear (Husked Ear Data Except When Stated Otherwise):

| | |
|---|---|
| Length: | 14 cm |
| Weight: | 111 gm |
| Mid-point Diameter: | 40 mm |
| Silk Color: | YELLOW |
| Husk Extension (Harvest stage): | MEDIUM (Barely Covering Ear) |
| Husk Leaf: | SHORT (<8 cm) |
| Taper of Ear: | SLIGHT |
| Position of Shank (dry husks): | UPRIGHT |
| Kernel Rows: | STRAIGHT DISTINCT |
| Husk Color (fresh): | LIGHT GREEN |
| Husk Color (dry): | BUFF |

TABLE 1-continued
VARIETY DESCRIPTION INFORMATION
INBRED = PHEM9

| | |
|---|---|
| Shank Length: | 13 cm |
| Shank (No. of internodes): | 7 |
| F. Kernel (Dried): | |
| Size (from ear mid-point) | |
| Length: | 10 mm |
| Width: | 9 mm |
| Thick: | 5 mm |
| Shape Grade (% rounds): | 20–40 (32% medium round based on Parent test Data) |
| Pericarp Color: | COLORLESS |
| Aleurone Color: | HOMOZYGOUS YELLOW |
| Endosperm Color: | YELLOW |
| Endosperm Type: | NORMAL STARCH |
| Gm Wt/100 Seeds (unsized): | 28 gm |
| G. Cob: | |
| Diameter at mid-point: | 23 mm |
| Strength: | STRONG |
| Color: | RED |
| H. Diseases: | |
| Corn Lethal Necrosis (MCMV = Maize Chlorotic Mottle Virus and MDMV = Maize Dwarf Mosaic Virus): | SUSCEPTIBLE |
| N. Leaf Blight (*E. turcicum*): | INTERMEDIATE |
| Common Rust (*P. sorghi*): | RESISTANT |
| Gray Leaf Spot (*C. zeae*): | SUSCEPTIBLE |
| Stewart's Wilt (*E. stewartii*): | RESISTANT |
| Goss's Wilt (*C. nebraskense*): | RESISTANT |
| Common Smut (*U. maydis*): | INTERMIDIATE |
| Head Smut (*S. reiliana*): | HIGHLY RESISTANT |
| Fusarium Ear Mold (*F. moniliforme*): | RESISTANT |
| I. Insects: | |
| European Corn Borer-1 Leaf Damage (Pre-flowering): | SUSCEPTIBLE |
| European Corn Borer-2 (Post-flowering): | SUSCEPTIBLE |
| The above descriptions are based on a scale of 1–9, 1 being highly susceptible, 9 being highly resistant. | |
| S (Susceptible): | Would generally represent a score of 1–3. |
| I (Intermediate): | Would generally represent a score of 4–5. |
| R (Resistant): | Would generally represent a score of 6–7. |
| H (Highly Resistant): | Would generally represent a score of 8–9. Highly resistant does not imply the inbred is immune. |
| J. Variety Most Closely Resembling: | |
| Character | Inbred |
| Maturity | PHJ40 |
| Usage | PHJ40 |

PHJ40 (PVP Certificate No. 8600133) is a Pioneer Hi-Bred International, Inc. proprietary inbred.
Data for Items B, C, D, E, F, and G is based primarily on a maximum of 6 reps from Johnston, Iowa grown in 1990, 1991, and 1992, plus description information from the maintaining station.

ELECTROPHORESIS RESULTS

Isozyme Genotypes for PHEM9

Isozyme data were generated for inbred corn line PHEM9 according to the procedures described in Stuber, C. W., Wendel, J. F., Goodman, M. M., and Smith, J. S. C., "Techniques and Scoring Procedures for Starch Gel Electrophoresis of Enzymes from Maize (*Zea mays* L.)", Technical Bulletin No. 286, North Carolina Agricultural Research Service, North Carolina State University, Raleigh, N.C. (1988).

The data in Table 2 compares PHEM9 with its parents, PHB49 and PHJ40.

TABLE 2
ELECTROPHORESIS RESULTS FOR PHEM9 AND ITS PARENTS PHB49 AND PHJ40

| | | PARENTS | |
|---|---|---|---|
| LOCI | PHEM9 | PHB49 | PHJ40 |
| ACP1 | 2 | 4 | 2 |
| ADH1 | 4 | 6 | 4 |
| CAT3 | 9 | 9 | 9 |
| DIA1 | 8 | 12 | 8 |
| GOT1 | 4 | 4 | 4 |
| GOT2 | 4 | 4 | 4 |
| GOT3 | 4 | 4 | 4 |
| IDH1 | 4 | 4 | 4 |
| IDH2 | 6 | 6 | 6 |
| MDH1 | 6 | 6 | 6 |
| MDH2 | 3.5 | 3.5 | 6 |
| MDH3 | 16 | 16 | 16 |
| MDH4 | 12 | 12 | 12 |
| MDH5 | 12 | 12 | 12 |
| MMM | 4 | 8 | 4 |
| PGM1 | 9 | 9 | 9 |
| PGM2 | 4 | 8 | 4 |

TABLE 2-continued

ELECTROPHORESIS RESULTS FOR PHEM9
AND ITS PARENTS PHB49 AND PHJ40

| LOCI | PHEM9 | PARENTS | |
|---|---|---|---|
| | | PHB49 | PHJ40 |
| PGD1 | 3.8 | 3.8 | 3.8 |
| PGD2 | 5 | 5 | 5 |
| PHI1 | 4 | 4 | 4 |

EXAMPLES

INBRED AND HYBRID PERFORMANCE OF PHEM9

In the examples that follow, the traits and characteristics of inbred corn line PHEM9 are given as a line in comparison with other inbreds and in hybrid combination. The data collected on inbred corn line PHEM9 is presented for the key characteristics and traits.

Table 3A compares PHEM9 to its PHB49 parent. PHEM9 has a better yield score than PHB49. PHEM9 is a taller inbred with higher ear placement and flowers (GDU Shed and GDU Silk) later than PHB49.

Table 3B compares PHEM9 to its PHJ40 parent. PHEM9 has significantly higher yield and grain harvest moisture, but lower test weight than PHJ40. PHEM9 is a taller inbred that flowers (GDU Shed and GDU Silk) later compared to PHJ40. PHEM9 has a higher early stand count and produces more tillers than PHJ40. PHEM9 has better staygreen and is slightly more resistant to first brood European corn borer than PHJ40.

Table 3C shows PHEM9 and PHT69 have similar yield, but PHEM9 has higher grain harvest moisture and lower test weight. PHEM9 is a shorter inbred with lower ear placement and flowers (GDU Shed and GDU Silk) slightly earlier than PHT69. PHEM9 has a greater pollen weight and larger tassel compared to PHT69. PHEM9 and PHT69 have similar stalk lodging resistance, but PHEM9 has significantly better root lodging resistance.

Table 3D results show PHEM9 and PHR47 have similar yield and test weight, but PHEM9 has a lower grain harvest moisture. PHEM9 is shorter inbred with lower ear placement and flowers (GDU Shed and GDU Silk) earlier than PHR47. PHEM9 has better grain appearance, but poorer staygreen and is more susceptible to northern leaf blight and second brood European corn borer compared to PHR47.

Table 4 compares PHEM9 to PHT69 when both were crossed to the same inbred testers. The PHEM9 hybrids are slightly higher yielding with higher grain harvest moisture and test weight than the PHT69 hybrids. The PHEM9 hybrids have better grain appearance and staygreen than the PHT69 hybrids. The PHEM9 hybrids are shorter in stature and have a lower ear placement than the PHT69 hybrids.

Table 5 compares PHEM9 to PHJ40 when both were crossed to the same inbred. The results show the PHEM9 hybrid has higher yield and grain harvest moisture than the PHJ40 hybrid. The PHEM9 hybrid is more susceptible to stalk lodging but has better root lodging resistance than the PHJ40 hybrid. The PHEM9 hybrid has better grain appearance and a higher early stand count compared to the PHJ40 hybrid. The PHEM9 hybrid is taller than the PHJ40 hybrid.

TABLE 3A

Figure 1:
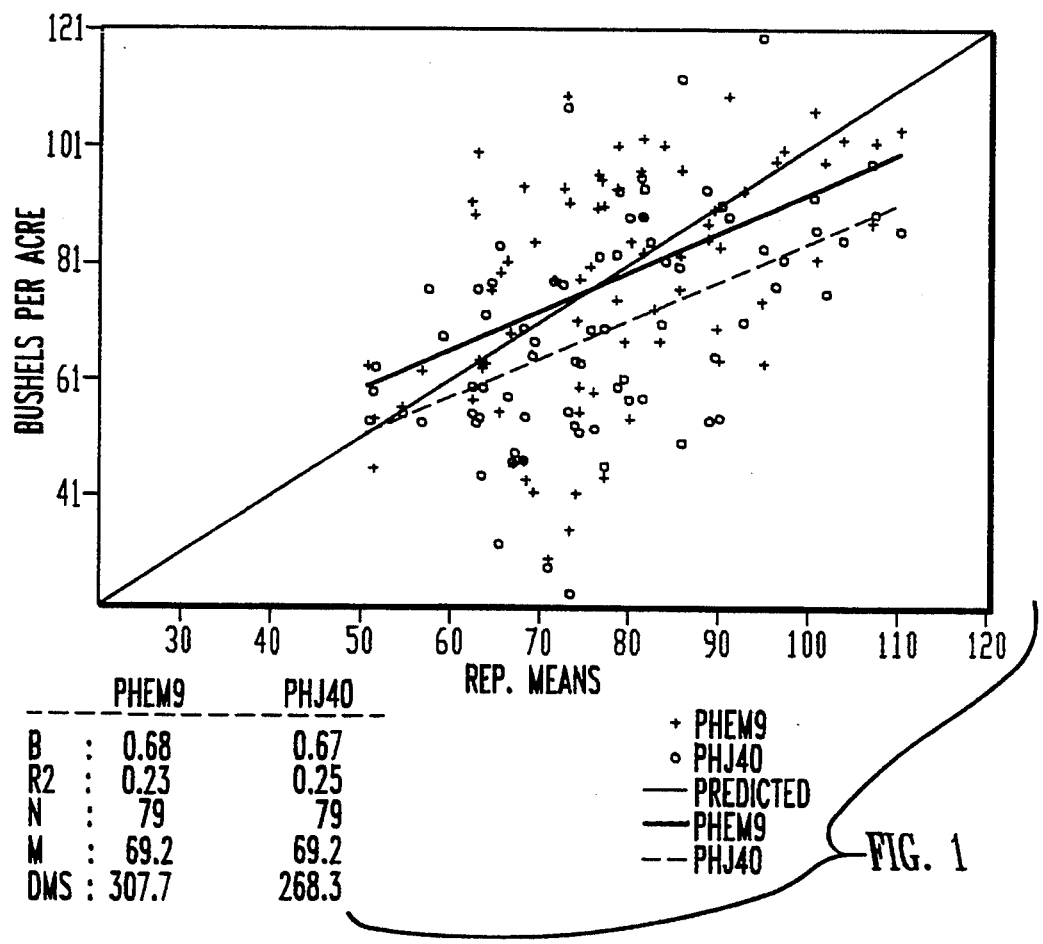
FIG. 1 compares the yield of PHEM9 and PHJ40. The PHEM9 inbred is higher yielding across all environments compared to PHJ40, but the inbreds have below average yield in high yield environments.
Figure 2:
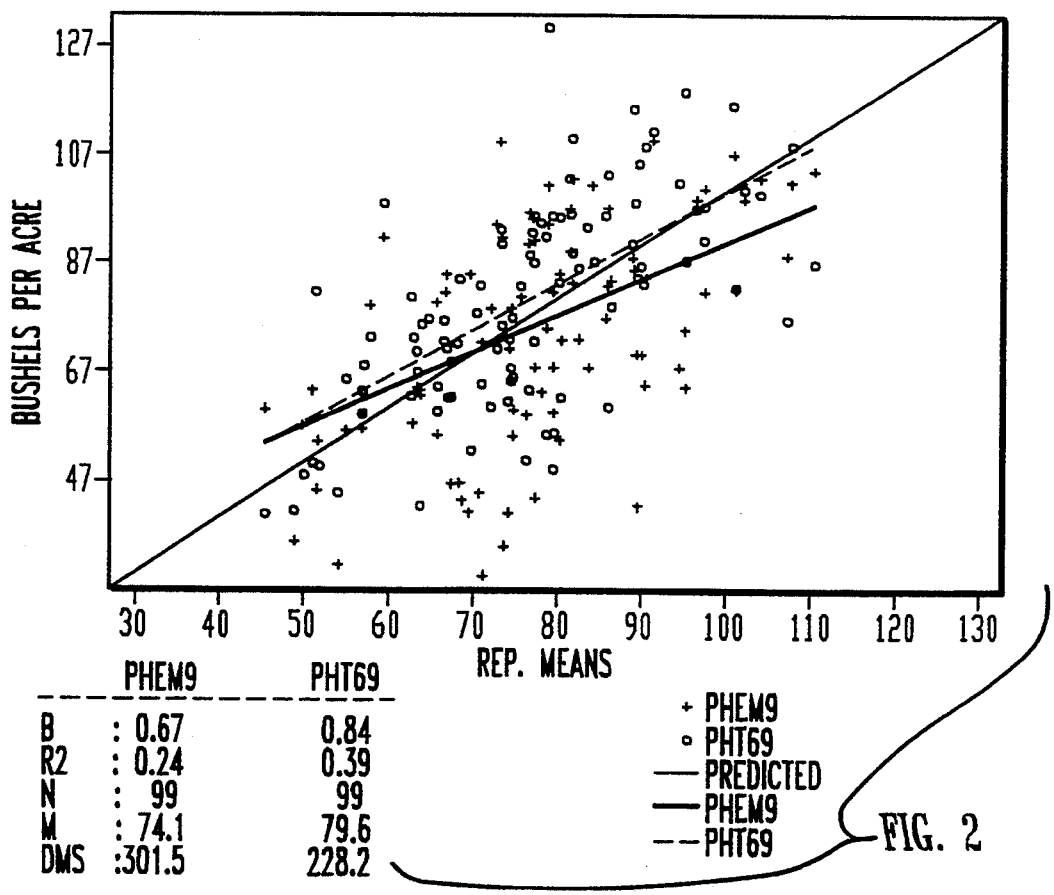
FIG. 2 compares the yield of PHEM9 and PHT69. PHEM9 has a yield disadvantage to PHT69 in all environments, but the differential is less in low yield environments. Both inbreds have above average yield in low yield environments but are slightly less than average in high yield environments.

PAIRED INBRED COMPARISON DATA
VARIETY #1 - PHEM9
VARIETY #2 - PHB49

| DEPT | VAR # | YLD SC ABS | EAR SZ ABS | BAR PLT ABS | PLT HT ABS | EAR HT ABS | SDG VGR ABS | EST CNT ABS | TIL LER ABS | GDU SHD ABS | GDU SLK ABS | TAS SZ ABS | TEX EAR ABS | SCT GRN ABS | ECB 1LF ABS |
|---|---|---|---|---|---|---|---|---|---|---|---|---|---|---|---|
| TOTAL SUM | 1 | 6.0 | 6.0 | 100.0 | 70.3 | 24.7 | 5.0 | 31.3 | 0.0 | 1273 | 1297 | 6.3 | 5.0 | 6.0 | 7.0 |
| | 2 | 4.0 | 5.0 | 100.0 | 65.3 | 17.7 | 5.0 | 33.0 | 0.0 | 1233 | 1263 | 4.7 | 5.0 | 6.0 | 3.0 |
| | LOCS | 1 | 1 | 1 | 3 | 3 | 1 | 3 | 2 | 3 | 3 | 3 | 1 | 1 | 1 |
| | REPS | 1 | 1 | 1 | 3 | 3 | 1 | 3 | 2 | 3 | 3 | 3 | 1 | 1 | 1 |
| | DIFF | 2.0 | 1.0 | 0.0 | 5.0 | 7.0 | 0.0 | 1.7 | 0.0 | 40 | 34 | 1.7 | 0.0 | 0.0 | 4.0 |
| | PROB | | | | .082* | .026+ | | .549 | 1.00 | .225 | .405 | .038+ | | | |

* = 10% SIG + = 5% SIG # = 1% SIG

TABLE 3B

PAIRED INBRED COMPARISON DATA
VARIETY #1 - PHEM9
VARIETY #2 - PHJ40

| DEPT | VAR # | BU ACR ABS | BU ACR %MN | YLD SC ABS | MST ABS | EAR SZ ABS | BAR PLT ABS | PLT HT ABS | EAR HT ABS | SDG VGR ABS | EST CNT ABS | DRP EAR ABS | TIL LER ABS | GDU SHD ABS | GDU SLK ABS | POL WT ABS |
|---|---|---|---|---|---|---|---|---|---|---|---|---|---|---|---|---|
| TOTAL SUM | 1 | 74.6 | 95 | 6.5 | 21.8 | 5.5 | 94.6 | 68.3 | 26.5 | 5.3 | 41.0 | 99.8 | 6.3 | 1261 | 1271 | 155.2 |
| | 2 | 64.3 | 82 | 6.1 | 17.9 | 5.0 | 94.7 | 62.6 | 26.3 | 5.3 | 38.6 | 99.8 | 1.5 | 1189 | 1201 | 109.0 |
| | LOCS | 30 | 30 | 14 | 34 | 8 | 31 | 46 | 46 | 41 | 92 | 17 | 38 | 67 | 58 | 8 |
| | REPS | 62 | 62 | 16 | 66 | 8 | 37 | 77 | 77 | 51 | 199 | 36 | 57 | 97 | 80 | 16 |
| | DIFF | 10.3 | 13 | 0.4 | 3.9 | 0.5 | 0.1 | 5.7 | 0.2 | 0.0 | 2.4 | 0.1 | 4.8 | 72 | 70 | 46.1 |
| | PROB | .000# | .000# | .336 | .000# | .170 | .954 | .000# | .684 | .833 | .000# | .649 | .019+ | .000# | .000# | .007# |
| | VAR | POL WT | POL SC | TAS BLS | TAS SZ EAR | TEX EAR | TST WT | GRN APP | SCT GRN | STA GRN | STK LDG | RT LDG | EAR MLD | NLF BLT | ECB 1LF | ECB 2SC |

TABLE 3B-continued

PAIRED INBRED COMPARISON DATA
VARIETY #1 - PHEM9
VARIETY #2 - PHJ40

| DEPT | # | % MN | ABS | ABS | ABS | ABS | ABS | ABS | ABS | ABS | ABS | ABS | ABS | ABS | ABS | ABS |
|---|---|---|---|---|---|---|---|---|---|---|---|---|---|---|---|---|
| TOTAL | 1 | 123 | 6.0 | 8.7 | 5.4 | 6.0 | 55.6 | 6.3 | 7.6 | 4.3 | 95.8 | 97.7 | 7.7 | 4.9 | 4.8 | 3.7 |
| SUM | 2 | 86 | 4.9 | 8.8 | 4.6 | 6.5 | 58.2 | 6.0 | 7.9 | 2.3 | 97.6 | 98.1 | 7.0 | 4.5 | 3.1 | 3.5 |
|  | LOCS | 8 | 23 | 5 | 19 | 8 | 30 | 20 | 14 | 19 | 18 | 8 | 14 | 11 | 22 | 12 |
|  | REPS | 16 | 36 | 9 | 22 | 8 | 62 | 41 | 16 | 32 | 38 | 17 | 16 | 13 | 30 | 22 |
|  | DIFF | 37 | 1.1 | 0.1 | 0.8 | 0.5 | 2.6 | 0.3 | 0.3 | 2.0 | 1.8 | 0.4 | 0.7 | 0.3 | 1.7 | 0.2 |
|  | PROB | .009# | .001# | .704 | .001# | .275 | .000# | .137 | .566 | .000# | .156 | .813 | .117 | .657 | .000# | .452 |

* = 10% SIG + = 5% SIG # = 1% SIG

TABLE 3C

PAIRED INBRED COMPARISON DATA
VARIETY #1 - PHEM9
VARIETY #2 - PHT69

| DEPT | VAR # | BU ACR ABS | BU ACR % MN | YLD SC ABS | MST ABS | EAR SZ ABS | BAR PLT ABS | PLT HT ABS | EAR HT ABS | SDG VGR ABS | EST CNT ABS |
|---|---|---|---|---|---|---|---|---|---|---|---|
| TOTAL | 1 | 72.0 | 94 | 6.6 | 20.3 | 5.7 | 94.1 | 68.9 | 27.2 | 5.4 | 43.4 |
| SUM | 2 | 76.6 | 100 | 6.7 | 18.7 | 6.4 | 95.4 | 79.0 | 32.0 | 5.4 | 36.9 |
|  | LOCS | 40 | 40 | 14 | 46 | 7 | 39 | 52 | 52 | 49 | 102 |
|  | REPS | 82 | 82 | 16 | 89 | 7 | 53 | 89 | 89 | 67 | 219 |
|  | DIFF | 4.7 | 6 | 0.1 | 1.6 | 0.7 | 1.3 | 10.2 | 4.9 | 0.0 | 6.5 |
|  | PROB | .111 | .147 | .793 | .000# | .008# | .375 | .000# | .000# | .940 | .000# |

| DEPT | VAR # | DRP EAR ABS | TIL LER ABS | GDU SHD ABS | GDU SLK ABS | POL WT ABS | POL WT % MN | POL SC ABS | TAS BLS ABS | TAS SZ ABS | TEX EAR ABS |
|---|---|---|---|---|---|---|---|---|---|---|---|
| TOTAL | 1 | 99.7 | 5.7 | 1268 | 1284 | 1552 | 123 | 6.1 | 8.7 | 5.4 | 6.0 |
| SUM | 2 | 99.7 | 4.0 | 1271 | 1305 | 1177 | 94 | 4.6 | 9.0 | 5.0 | 5.1 |
|  | LOCS | 22 | 44 | 68 | 58 | 8 | 8 | 22 | 5 | 18 | 7 |
|  | REPS | 46 | 69 | 100 | 81 | 16 | 16 | 34 | 9 | 20 | 7 |
|  | DIFF | 0.1 | 1.7 | 03 | 21 | 375 | 29 | 1.5 | 0.3 | 0.4 | 0.9 |
|  | PROB | .682 | .316 | .572 | .001# | .027+ | .023+ | .000# | .208 | .042+ | .078* |

| DEPT | VAR # | TST WT ABS | GRN APP ABS | SCT GRN ABS | STA GRN ABS | STK LDG ABS | RT LDG ABS | EAR MLD ABS | NLF BLT ABS | STW WLT ABS | ECB 1LF ABS | ECB 2SC ABS |
|---|---|---|---|---|---|---|---|---|---|---|---|---|
| TOTAL | 1 | 56.4 | 6.3 | 7.5 | 3.5 | 93.6 | 98.5 | 7.8 | 4.5 | 6.0 | 4.7 | 3.1 |
| SUM | 2 | 57.8 | 6.3 | 7.3 | 3.4 | 92.2 | 91.2 | 7.7 | 4.4 | 3.0 | 6.5 | 3.7 |
|  | LOCS | 41 | 28 | 13 | 24 | 30 | 12 | 12 | 14 | 1 | 26 | 21 |
|  | REPS | 84 | 57 | 15 | 43 | 62 | 24 | 14 | 20 | 1 | 40 | 42 |
|  | DIFF | 1.4 | 0.0 | 0.2 | 0.0 | 1.4 | 7.2 | 0.1 | 0.1 | 3.0 | 1.9 | 0.5 |
|  | PROB | .000# | .909 | .673 | .957 | .492 | .036+ | .886 | .749 |  | .000# | .207 |

* = 10% SIG + = 5% SIG # = 1% SIG

TABLE 3D

PAIRED INBRED COMPARISON DATA
VARIETY #1 - PHEM9
VARIETY #2 - PHR47

| DEPT | VAR # | BU ACR ABS | BU ACR % MN | YLD SC ABS | MST ABS | EAR SZ ABS | BAR PLT ABS | PLT HT ABS | EAR HT ABS | SDG VGR ABS | EST CNT ABS | DRP EAR ABS | TIL LER ABS | GDU SHD ABS | GDU SLK ABS |
|---|---|---|---|---|---|---|---|---|---|---|---|---|---|---|---|
| TOTAL | 1 | 57.9 | 89 | 6.3 | 16.2 | 5.3 | 93.6 | 66.4 | 26.3 | 5.8 | 31.1 | 99.3 | 9.9 | 1278 | 1292 |
| SUM | 2 | 61.1 | 91 | 6.0 | 17.6 | 6.0 | 89.7 | 79.0 | 32.1 | 4.8 | 29.6 | 100.0 | 1.6 | 1407 | 1431 |
|  | LOCS | 6 | 6 | 7 | 7 | 3 | 13 | 18 | 18 | 26 | 50 | 3 | 15 | 37 | 35 |
|  | REPS | 12 | 12 | 9 | 13 | 3 | 17 | 32 | 32 | 32 | 128 | 6 | 18 | 52 | 50 |
|  | DIFF | 3.1 | 1 | 0.3 | 1.4 | 0.7 | 3.9 | 12.6 | 5.8 | 1.0 | 1.5 | 0.8 | 8.3 | 129 | 139 |
|  | PROB | .696 | .907 | .654 | .077* | .635 | .109 | .000# | .001# | .002# | .008# | .195 | .095* | .000# | .000# |

| DEPT | VAR # | POL SC ABS | TAS BLS ABS | TAS SZ ABS | TEX EAR ABS | TST WT ABS | GRN APP ABS | SCT GRN ABS | STA GRN ABS | STK LDG ABS | RT LDG ABS | EAR MLD ABS | NLF BLT ABS | STW WLT ABS | ECB 1LF ABS | ECB 2SC ABS |
|---|---|---|---|---|---|---|---|---|---|---|---|---|---|---|---|---|
| TOTAL | 1 | 5.9 | 9.0 | 5.4 | 6.0 | 57.7 | 6.6 | 6.7 | 3.0 | 97.3 | 100.0 | 7.4 | 4.8 | 6.0 | 5.1 | 2.8 |
| SUM | 2 | 5.9 | 9.0 | 5.7 | 5.3 | 56.4 | 6.0 | 5.5 | 6.4 | 96.5 | 89.5 | 7.6 | 5.8 | 4.0 | 4.5 | 5.2 |
|  | LOCS | 7 | 1 | 7 | 3 | 6 | 6 | 6 | 8 | 4 | 1 | 7 | 6 | 1 | 13 | 9 |
|  | REPS | 10 | 1 | 9 | 3 | 12 | 11 | 8 | 12 | 8 | 1 | 9 | 6 | 1 | 13 | 14 |
|  | DIFF | 0.0 | 0.0 | 0.3 | 0.7 | 1.4 | 0.6 | 1.2 | 3.4 | 0.7 | 10.5 | 0.1 | 1.0 | 2.0 | 0.5 | 2.4 |
|  | PROB | .000# |  | .356 | .184 | .114 | .034+ | .110 | .007# | .825 |  | .788 | .041+ |  | .237 | .002# |

* = 10% SIG + = 5% SIG # = 1% SIG

TABLE 4

AVERAGE INBRED BY TESTER PERFORMANCE COMPARING PHEM9 TO PHT69 CROSSED TO THE SAME INBRED TESTERS AND GROWN IN THE SAME EXPERIMENTS. ALL VALUES ARE EXPRESSED AS PERCENT OF THE EXPERIMENT MEAN EXCEPT PREDICTED RM, SELECTION INDEX, AND YIELD (BU/ACR).

|  |  | PRM | SEL IND | BU ACR | YLD | MST | GDU SHD | PRM SHD | STK LDG | RT LDG |
|---|---|---|---|---|---|---|---|---|---|---|
| TOTAL | REPLIC. | 76 | 75 | 75 | 75 | 76 | 22 | 9 | 51 | 5 |
| MEAN WTS | PHEM9 | 97 | 103 | 140 | 103 | 106 | 101 | 96 | 101 | 102 |
| MEAN WTS | PHT69 | 96 | 102 | 138 | 101 | 103 | 100 | 94 | 100 | 102 |
|  | DIFF. | 1 | 2 | 1 | 2 | 4 | 2 | 1 | 1 | 1 |

|  |  | STA GRN | TST WTA | GRN APP | SDG VGR | EST CNT | STK CNT | PLT HT | EAR HT | DRP EAR | BRT STK |
|---|---|---|---|---|---|---|---|---|---|---|---|
| TOTAL | REPLIC. | 3 | 74 | 17 | 39 | 46 | 100 | 34 | 34 | 33 | 8 |
| MEAN WTS | PHEM9 | 134 | 101 | 96 | 96 | 102 | 102 | 101 | 103 | 100 | 100 |
| MEAN WTS | PHT69 | 92 | 99 | 94 | 107 | 101 | 101 | 104 | 106 | 100 | 100 |
|  | DIFF. | 42 | 1 | 1 | 11 | 1 | 1 | 4 | 3 | 0 | 0 |

TABLE 5

VARIETY #1 - PHEM9 HYBRID
VARIETY #2 - PHJ40 HYBRID

| DEPT | VAR # | PRM | PRM SHD | BU ACR ABS | BU ACR % MN | MST % MN | STK LDG % MN | RT LDG % MN | STA GRN % MN | TST WTA % MN |
|---|---|---|---|---|---|---|---|---|---|---|
| TOTAL SUM | 1 | 89 | 90 | 133.9 | 103 | 97 | 100 | 105 | 80 | 100 |
|  | 2 | 87 | 87 | 128.6 | 99 | 92 | 104 | 77 | 81 | 101 |
|  | LOCS | 19 | 15 | 62 | 62 | 64 | 58 | 7 | 16 | 64 |
|  | REPS | 19 | 15 | 116 | 116 | 120 | 108 | 14 | 30 | 120 |
|  | DIFF | 3 | 3 | 5.3 | 4 | 5 | 3 | 28 | 2 | 0 |
|  | PROB | .000# | .000# | .005# | .013+ | .000# | .018+ | .065* | .744 | .260 |

| DEPT | VAR # | GRN APP % MN | SDG VGR % MN | EST CNT % MN | STK CNT % MN | PLT HT % MN | EAR HT % MN | DRP EAR % MN | BRT STK % MN | GDU SHD % MN |
|---|---|---|---|---|---|---|---|---|---|---|
| TOTAL SUM | 1 | 95 | 99 | 101 | 100 | 100 | 95 | 99 | 92 | 100 |
|  | 2 | 89 | 96 | 99 | 100 | 96 | 96 | 100 | 100 | 97 |
|  | LOCS | 54 | 43 | 43 | 72 | 43 | 43 | 31 | 3 | 26 |
|  | REPS | 104 | 73 | 86 | 134 | 77 | 77 | 55 | 6 | 56 |
|  | DIFF | 6 | 3 | 2 | 0 | 4 | 1 | 1 | 8 | 3 |
|  | PROB | .019+ | .406 | .009# | .962 | .000# | .510 | .277 | .132 | .000# |

* = 10% SIG + = 5% SIG # = 1% SIG

INDUSTRIAL APPLICABILITY

The foregoing is set forth by way of example and is not intended to limit the scope of the invention.

This invention also is directed to methods for producing a corn plant by crossing a first parent corn plant with a second parent corn plant wherein the first or second parent corn plant is an inbred corn plant from the line PHEM9. Further, both first and second parent corn plants can come from the inbred corn line PHEM9. Thus, any such methods using the inbred corn line PHEM9 are part of this invention: selfing, backcrosses, hybrid production, crosses to populations, and the like. It also would include more unconventional methods of combining the inbred with another, such as using various culturing techniques known to those skilled in the art. All plants produced using inbred corn line PHEM9 as a parent are within the scope of this invention. Advantageously, the inbred corn line is used in crosses withother, different, corn inbreds to produce first generation (F$_1$) corn hybrid seeds and plants with superior characteristics.

As used herein, the term plant includes plant cells, plant protoplasts, plant cell tissue cultures from which corn plants can be regenerated, plant calli, plant clumps, and plant cells that are intact in plants or parts of plants, such as embryos, pollen, flowers, kernels, ears, cobs, leaves, husks, stalks, roots, root tips, anthers, silk and the like.

Duncan, Williams, Zehr, and Widholm, *Planta*, (1985) 165:322–332 reflects that 97% of the plants cultured which produced callus were capable of plant regeneration. Subsequent experiments with both inbreds and hybrids produced 91% regenerable callus which produced plants. In a further study in 1988, Songstad, Duncan & Widholm in *Plant Cell Reports* (1988), 7:262–265 reports several media additions which enhance regenerability of callus of two inbred lines. Other published reports also indicated that "nontraditional" tissues are capable of producing somatic embryogenesis and plant regeneration. K. P. Rao, et al., *Maize Genetics Cooperation Newsletter*, 60:64–65 (1986), refers to somatic embryogenesis from glume callus cultures and B. V. Conger, et al., *Plant Cell Reports*, 6:345–347 (1987) indicates somatic embryogenesis from the tissue cultures of maize leaf segments. Thus, it is clear from the literature that the state of the art is such that these methods of obtaining plants are, and were, "conventional" in the sense that they are routinely used and have a very high rate of success.

Tissue culture of corn is described in European Patent Application, publication 160,390, incorporated herein by reference. Corn tissue culture procedures are also described in Green and Rhodes, "Plant Regeneration in Tissue Culture of Maize," *Maize for Biological*

*Research* (Plant Molecular Biology Association, Charlottesville, Va. 1982, at 367–372) and in Duncan, et al., "The Production of Callus Capable of Plant Regeneration from Immature Embryos of Numerous *Zea Mays* Genotypes," 165 *Planta* 322–332 (1985). Thus, another aspect of this invention is to provide cells which upon growth and differentiation produce corn plants having the physiological and morphological characteristics of the inbred line PHEM9.

Corn is used as human food, livestock feed, and as raw material in industry. The food uses of corn, in addition to human consumption of corn kernels, include both products of dry- and wet-milling industries. The principal products of corn dry milling are grits, meal and flour. The corn wet-milling industry can provide corn starch, corn syrups, and dextrose for food use. Corn oil is recovered from corn germ, which is a by-product of both dry- and wet-milling industries.

Corn, including both grain and non-grain portions of the plant, is also used extensively as livestock feed, primarily for beef cattle, dairy cattle, hogs, and poultry.

Industrial uses of corn are mainly from corn starch in the wet-milling industry and corn flour in the dry-milling industry. The industrial applications of corn starch and flour are based on functional properties, such as viscosity, film formation, adhesive properties, and ability to suspend particles. The corn starch and flour have application in the paper and textile industries. Other industrial uses include applications in adhesives, building materials, foundry binders, laundry starches, explosives, oil-well muds, and other mining applications.

Plant parts other than the grain of corn are also used in industry. Stalks and husks are made into paper and wallboard and cobs are used for fuel and to make charcoal.

The seed of inbred corn line PHEM9, the plant produced from the inbred seed, the hybrid corn plant produced from the crossing of the inbred, hybrid seed, and various parts of the hybrid corn plant can be utilized for human food, livestock feed, and as a raw material in industry.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. Inbred corn seed designated PHEM9 and having ATCC Accession No. 75642.
2. A corn plant produced by the seed of claim 1.
3. A tissue culture of regenerable cells of a plant according to claim 2 wherein the tissue regenerates plants having all of the physiological and morphological characteristics of PHEM9.
4. A corn plant regenerated from the tissue culture of claim 3.
5. A tissue culture according to claim 3, the tissue culture initiated from the group consisting of leaves, pollen, embryos, roots, root tips, anthers, silk, flowers, kernels, ears, cobs, husks, stalks, or cells thereof.
6. A tissue culture according to claim 3, the tissue culture comprising protoplasts.

* * * * *